(12) United States Patent
Meseguer Navarro et al.

(10) Patent No.: US 9,523,690 B2
(45) Date of Patent: Dec. 20, 2016

(54) BIOMARKERS FOR THE DIAGNOSIS AND/OR PROGNOSIS OF CLEAR CELL RENAL CELL CARCINOMA

(71) Applicant: FUNDACIÓ HOSPITAL UNIVERSITARI VALL D'HEBRON—INSTITUT DE RECERCA, Barcelona (ES)

(72) Inventors: Anna Meseguer Navarro, Barcelona (ES); Thais Cuadros Arasa, Barcelona (ES)

(73) Assignee: FUNDACIÓ HOSPITAL UNIVERSITARI VALL D'HEBRON-INSTITUT DE RECERCA, Barcelona (ES)

( * ) Notice: Subject to any disclaimer, the term of this patent is extended or adjusted under 35 U.S.C. 154(b) by 0 days.

(21) Appl. No.: 14/427,285

(22) PCT Filed: Sep. 12, 2013

(86) PCT No.: PCT/EP2013/068896
  § 371 (c)(1),
  (2) Date: Mar. 10, 2015

(87) PCT Pub. No.: WO2014/041064
  PCT Pub. Date: Mar. 20, 2014

(65) Prior Publication Data
  US 2015/0219660 A1  Aug. 6, 2015

(30) Foreign Application Priority Data

Sep. 13, 2012 (EP) .................... 12382350

(51) Int. Cl.
  *G01N 33/574* (2006.01)
(52) U.S. Cl.
  CPC . *G01N 33/57438* (2013.01); *G01N 2333/4706* (2013.01); *G01N 2800/52* (2013.01)
(58) Field of Classification Search
  CPC .............. G01N 33/57438; G01N 2333/4706; G01N 2800/52
  See application file for complete search history.

(56) References Cited

U.S. PATENT DOCUMENTS

2003/0012788 A1*  1/2003  Renauld et al. ....... C07K 14/54
                                                          424/145.1

OTHER PUBLICATIONS

Aggarwal et al., 2006. Targeting signal-transducer-and-activator-of-transcription-3 for prevention and therapy of cancer. Ann. N.Y. Acad. Sci. 1091: 151-169.*
Cell Signaling Technology, Cat #9134. Phospho-Stat3 (Ser727) Antibody Product Sheet, revised Nov. 17, 2015.*
Decker et al., 2000. Serine phosphorylation of STATs. Oncogene 19: 2628-2637.*
Xie et al., 2000. Interleukin (IL)-22, a novel human cytokine that signals through the interferon receptor-related proteins CRF-2 and IL22R. J. Biol. Chem. 275: 31335-31339.*
International Search Report and Written Opinion dated Jan. 17, 2014, in PCT/EP2013/068896, 13 pages.
Altschul et. al., "Gapped BLAST and PSI-BLAST: a new generation of protein database search programs", Nucleic Acids Research vol. No. 25, pp. 3389-3402 (1997).
Cuadros et al., "Hepatitis A virus cellular receptor 1/kidney injury molecule-1 is a susceptibility gene for clear cell renal cell carcinoma and hepatitis A virus cellular receptor/kidney injury molecule-1 ectodomain shedding a predictive biomarker of tumour progression", European Journal of Cancer, vol. 49, No. 8, May 1, 2013 pp. 2034-2047.
Detre et al., "A "quickscore" method for immunohistochemical semiquantitation: validation for estrogen receptor in breast carcinomas", J. Clin. Pathol. vol. No. 48, pp. 876-878 (1995).
Dong et al.,"Expression and clinical significance of kidney injury molecule-1A in renal epithelial neoplasms", Zhonghua Bing Li Xue Za Zhi, vol. 39, No. 1, Jan. 1, 2010, pp. 35-39. (English Abstract Provided).
Dudka et al., "STAT3 Binding To The Fgf Receptor Is Activated By Receptor Amplification", Cancer Res. vol. No. 70(8), pp. 3391-3401(2010).
Guo et al., "Activation of STAT3 in renal tumors", Am. J. Transl Res. vol. 1(3), pp. 283-290 (2009).
Hazan-Halevy et al., "STAT3 is constitutively phosphorylated on serine 727 residues, binds DNA, and activates transcription in CLL cells", Blood vol. 115 (14), pp. 2852-2863 (2010).
Horiguchi et al., "Activation of Signal Transducer and Activator of Transcription 3 in Renal Cell Carcinoma: A Study of Incidence and Its Association With Pathological Features and Clinical Outcome", Journal of Urology, Lippincott Williams & Wilkins, Baltimore, MO, US, vol. 168, No. 2, Aug. 1, 2002, pp. 762-765.
Komohara et al., "Macrophage infiltration and its prognostic relevance in clear cell renal cell carcinoma", Cancer Science vol. 102, No. 7, May 9, 2011, pp. 1424-1431.
Lin et al., "Human Kidney Injury Molecule-1 (hKIM-1): A useful Immunohistochemical Marker for Diagnosing Renal Cell Carcinoma and Ovarian Clear Cell Carcinoma", Am. J. Surg. Pathol; 31, pp. 371-381 (2007).
Oosterwijk, et al., "Monoclonal antibody G 250 recognizes a determinant present in renal-cell carcinoma and absent from normal kidney", Int. Journal of Cancer vol. No. 38; pp. 489-494 (1986).
Sangoi et al., "Immunohistochemical Distinction of Primary Adrenal Cortical Lesions From Metastatic Clear Cell Renal Cell Carcinoma: A Study of 248 Cases", Am. J. Surg Pathol. vol. No. 35(5), pp. 678-686 (2011).

(Continued)

*Primary Examiner* — Jacob Cheu
(74) *Attorney, Agent, or Firm* — Squire Patton Boggs (US) LLP

(57) ABSTRACT

The present invention provides an in vitro method for the diagnosis and/or prognosis of clear cell Renal Cell Carcinoma in a subject suspected of suffering it, in which method the presence and levels of a phosphorylated form of the protein Signal transducer and activator of transcription 3 (STAT3) are determined. Said determination is performed in any isolated sample, in particular in a biopsy of a tumor. The invention relates also to the use of means for detecting said phosphorylated form to be applied in the method for the diagnosis and/or prognosis of clear cell Renal Cell Carcinoma.

13 Claims, 2 Drawing Sheets

(56) References Cited

OTHER PUBLICATIONS

Vacas et al., "Vasoactive intestinal peptide (VIP) inhibits human renal cell carcinoma proliferation", Biochimica Et Biophysica Acta (BBA)—Molecular Cell Research, vol. 1823, No. 10, Jun. 21, 2012, pp. 1676-1685.

Van Diest et al., "A scoring system for immunohistochemical staining: consensus report of the task force for basic research of the EORTC—GCCG", J. Clin. Pathol. vol. 50, Oct. 1, 1997, pp. 801-804.

Wen et al., "Maximal activation of 1 transcription by Stat1 and Stat3 requires both tyrosine and serine phosphorylation", Cell, Cell Press, US, vol. 82, Jul. 28, 1995, pp. 241-250.

\* cited by examiner

BIOMARKERS FOR THE DIAGNOSIS AND/OR PROGNOSIS OF CLEAR CELL RENAL CELL CARCINOMA

CROSS-REFERNCE TO RELATED APPLICATIONS

This application is the National Stage of International Patent Application No. PCT/EP2013/068896, which claims the benefit of EP Application No. 12382350.2, filed Sep. 13, 2012, each of which is incorporated by reference in its entirety.

SEQUENCE LISTING

This application contains a Sequence Listing which has been submitted electronically in ASCII file format and is hereby incorporated by reference in its entirety. Said ASCII file, created on Mar. 8, 2015, is named 108663_P2433US00.txt and is 13,966 bytes size.

The present invention relates to the field of medicine, in particular in the field of cancer detection and prosecution. It provides methods for the diagnosis and/or prognosis of cancers, namely renal cancers.

BACKGROUND ART

Clear cell Renal Cell Carcinoma (ccRCC) represents the most prevalent subtype of Renal Cell Carcinoma, and was initially known as granular cell tumour, Grawitz tumour or hypernephrome.

ccRCC is an isolated and malignant lesion, which originates in the renal cortex. Renal proximal tubule cells are considered as the cell originating this type of malignant neoplasm. A rigorous examination shows the presence of a yellowish, round and well-defined lesion with multifocal hemorrhages and necrosis.

One of the major features of ccRCC is that it appears without specific symptoms and at least ⅓ of the patients have already a metastatic pattern at the time of diagnosis. Thus, ccRCC implies a great variety of non-specific clinical manifestations, going from the broadly known hematuria, pain and detectable renal mass, to the more complex paraneoplastic syndrome. Thus, the most common way to detect renal cell carcinomas in general is accidentally, during the performance of other diagnostic tests.

Nowadays, ccRCC are finally diagnosed from the visual analysis of biopsies of the kidney, or by means of ecography tools.

Biopsies are characterized by morphological cell features. ccRCC react with the antibody known as RCC disclosed by E. Oosterwdk, et al., "Monoclonal antibody G 250 recognizes a determinant present in renal-cell carcinoma and absent from normal kidney", *Int Journal of Cancer*—1986, Vol. No. 38; pp. 489-494, which allows the distinction between metastatic lesions with clear cell features. Other immunostainings include the use of CD10, which is a glycoprotein that is particularly abundant in kidney, where it is present on the brush border of proximal tubules and on glomerular epithelium, and cytokeratins.

The patients can be treated by surgery being submitted to total or partial nephrectomy (kidney extirpation). Alternatively, patients are submitted to chemotherapeutic treatments with the multi-targeted receptor tyrosine kinase (RTK) inhibitor sunitinib of Pfizer.

An additional drawback of this type of cancer is that it may evolve to a worse or bad outcome (prognosis) depending on multifactor causes and because some patients are resistant to the treatments.

Thus, in case that a chemotherapeutical approach is to be applied, or a nephrectomy cannot be suggested for example due to possible complications derived from the patients profile (diabetes, advanced age, cardiovascular problems, etc.), the percentage of survival in case of ccRCC is low.

There is a need not only of specific markers for the diagnosis of ccRCC, but also of markers that can predict the prognosis of the disease. The definition of the outcome (prognosis) of ccRCC is of special interest in order to face the disease or to apply a correct therapy as soon as possible although other aspects of the health of the patients can be compromised.

At this regard, one of the tools employed for the prediction of the outcome of ccRCC is the Fuhrman system, in which each pathological level of the disease is defined by means of the nuclear features of the cells under study as follows: Grade I, cells have uniform and small nucleus; Grade II, cells with an open granular chromatin without evident nucleolus; Grade III, exacerbate nucleolus are identified; and Grade IV, defined by the presence of macronucleolus and of nuclear pleomorphism. The highest level identified in a specific lesion is the one determining the level of RCC.

Survival of patients diagnosed of ccRCC is well-correlated with the pathological level or grade. Thus, a great pathological level identified according to the Fuhrman grade, for example, is characterized by great-size tumours, extending through the renal vein or to perirenal fat. Metastasis of ccRCC is usually focused to the lung, bone and lymphatic nodes. Other less common invasion profiles include thyroid, heart spleen and pancreas, but only in cases of very disseminated ccRCC.

There exist several biochemical studies which try to correlate some molecules with the prognosis of renal neoplasms. Thus, in Guo et al., "Activation of STAT3 in renal tumors", *Am. J. Transl Res*—2009, vol. 1(3), pp.: 283-290, it is disclosed that the transcription factor STAT3 is phosphorylated at the tyrosine residue Tyr705 in the 59.5% of ccRCC, and is also indicated as worse prognosis biomarker of renal neoplasms.

The document of Horiguchi et al., "Activation of signal transducer and activator of transcription 3 in renal cell carcinoma: A study of incidence and its association with pathological features and clinical outcome", *The Journal of Urology*—2002, Vol. 168, pp. 762-765, is another example of document in which the STAT3 phosphorylated at the tyrosine residue Tyr705 is indicative of poor prognosis in case of renal cell carcinoma. In this document the authors indicate that a significant association of high levels of p-STAT3 correlated with metastasis, but no significant associations of p-STAT3 immunostaining with pathological stage or grade were observed. In this document tissue immunostaining is performed by pathologist classifying the activation of STAT3 in low or high based on the positive nuclear staining.

On the other hand, in the document of Komohara et al. "Macrophage infiltration and its prognostic relevance in clear cell renal cell carcinoma", *Japanese Cancer Association*—2011, Vol. 102(4), pp.: 1424-1431, it is proposed to investigate a type of tumor-associated macrophages as markers for determining the outcome of ccRCC.

Finally, Kidney Injury Molecule 1 (KIM-1) has also been assessed to predict the outcome of different types of renal carcinomas, including ccRCC. An example of this is exposed in the document of Dong et al., "Expression and clinical significance of Kidney Injury Molecule 1 in renal epithelial neoplasms, PUBMED 20368397, Zhonguabing-2010,Vol. 39(1), pp. 35-39. The molecule, detectable by immunostaining, is presented as a usable more precise tool for histological classification and for a more accurate diagnosis.

Although there are some tools, indicia and markers for the diagnosis of ccRCC, and also there exist systems for determining the prognosis or outcome of the disease, alternative methods and tools are needed for providing more specific, sensitive and meaningful data at the same time they are methods or tools easy to be applied.

SUMMARY OF THE INVENTION

Deeply studying isolated samples of subjects diagnosed of clear cell Renal Cell Carcinoma (ccRCC), it has been surprisingly found that the transcription factor known as Signal transducer and activator of transcription 3 (STAT3) is highly phosphorylated in some residues in those subjects which, a part of being diagnosed of ccRCC, have a worse outcome of the disease or bad prognosis.

Thus, in a first aspect the invention relates to an in vitro method for the diagnosis and/or prognosis of clear cell Renal Cell Carcinoma in a subject suspected of suffering it, comprising the step of detecting in an isolated sample of the subject, the presence of the Signal transducer and activator of transcription 3 (STAT3), which comprises the amino acid sequence SEQ ID NO:1
DATNILVXPL
wherein X means a phosphorylated serine residue.

This aspect can be generalyzed to in vitro methods for the diagnosis and/or prognosis of clear cell carcinomas in a subject suspected of suffering it, said methods comprising the step of detecting in an isolated sample of the subject the presence of a protein Signal transducer and activator of transcription 3 (STAT3), which comprises the amino acid sequence SEQ ID NO:1
DATNILVXPL
wherein X means a phosphorylated serine residue. Examples of clear cell carcinomas include clear cell sarcomas, and clear cell adenocarcinomas, this later comprising clear cell adenocarcinoma of the vagina, clear cell renal cell carcinomas, clear cell ovarian carcinoma, uterine clear cell carcinoma, clear cell carcinoma of the lung, clear cell adenocarcinoma of the lung, and clear cell squamous cell carcinoma of the lung.

In the present invention, STAT3 comprising the amino acid sequence SEQ ID NO:1 being phosporylated in the serine (Ser) residue, is also mentioned as serine phosphorylated STAT3 (P-Ser-STAT3).

As will be illustrated in the examples below, the detection of the protein comprising such a sequence is indicative of ccRCC and of bad prognosis.

The mammalian protein STAT3 comprising phosphorylated serine residues along its entire sequence has been disclosed in documents such as Dudka et al., "STAT3 BINDING TO THE FGF RECEPTOR IS ACTIVATED BY RECEPTOR AMPLIFICATION", *Cancer Res.*—2010, Vol. No. 70(8), pp.: 3391-3401.

This document discloses the role of human STAT3 in the cell tumour processes, which cells are over-expressing the fibroblast growing factor receptor. Although in this document assays are included to elucidate the role of the protein carrying a phosphorylated serine at the position 727 (Ser 727), no concluding data are provided, and no correlation0 with cancer is indicated.

On the other hand, the document Hazan-Halevy et al., "STAT3 is constitutively phosphorylated on serine 727 residues, binds DNA, and activates transcription in CLL cells", Blood-2010 vol. 115 (14), pp.: 2852-2863, discloses that said serine residue is phosphorylated in cases of other cancer type, namely in the Chronic Lymphocytic Leukaemia (CLL). However, no data are depicted with regard to the prognosis of the diseases.

Another document disclosing phosphorylated STAT3, although not specifically disclosing the phosphorylated residue, is the one of Vacas et al., "Vasoactive Intestinal Peptide (VIP) inhibits human renal cell carcinoma proliferation", Biochimica et Biophysica Acta-2012, Vol 1823, pp.: 1676-1685. In this document the phosphorylated STAT3 is used as maker of cell proliferation in an assay in which different cell lines are tested before VIP. Again, no data are depicted with regard to the prognosis of ccRCC.

A second aspect of the invention is a method of deciding or recommending whether to initiate a medical regimen of a subject suspected of suffering clear cell Renal Cell Carcinoma, which method comprises the steps of:
a) detecting, in vitro in an isolated sample of the subject, the presence of the Signal transducer and activator of transcription 3 (STAT3), which comprises the amino acid sequence SEQ ID NO:1; and
b) diagnosing and/or determining a bad prognosis of clear cell Renal Cell Carcinoma if the protein comprising SEQ ID NO: 1 is detected;
wherein:
if the subject is diagnosed of clear cell Renal Cell Carcinoma and determined as bad prognosis, then a surgical intervention in which a partial or total nephrectomy is recommended; or
if the patient is diagnosed of not suffering clear cell Renal Cell Carcinoma or is diagnosed of clear cell Renal Cell Carcinoma of good prognosis, a medical regimen selected from the group consisting of partial nephrectomy, follow-up, chemotherapy, and combinations thereof is recommended.

The method for deciding or recommending a specific medical regimen is of special relevance when the subject diagnosed of ccRCC has a level of the pathology (pathological stage) that firstly would be catalogued as not critical according to the morphological parameters of the tumour, or as not advisable to be excised, but having to be catalogued as bad prognosis according to the levels of P-Ser-STAT3, that is, the levels of the Signal transducer and activator of transcription 3 (STAT3), which comprises the amino acid sequence SEQ ID NO:1.

That is, according to current clinical protocols, some patients diagnosed of ccRCC, in which the size of the detected tumour is considered of small size 4 cm of diameter), are not submitted to nephrectomy (total or partial). This is so because in function of the conditions of the subject (advanced age, cardio-vascular problems, diabetes, etc.), extirpation of the tumour involves a risk higher than the risk of metastasis or of development of the tumour. In these specific cases, the facultative encourages a deep follow-up of the patient and applies alternative treatments (including chemotherapy).

This method of deciding or recommending a specific medical regimen of the invention can also be generalized to methods for deciding or recommending a specific medical regimen in subjects suspected of suffering clear cell carcinomas.

With the methods of the invention, a new marker for the prognosis of ccRCC is provided, independently of the markers or systems actually being used (Fuhrman grade system, Group of Risk and Clinical Stage). Thus, the detection in a sample of the subject of STAT3 comprising the sequence SEQ ID NO: 1 (P-Ser-STAT3) in which the serine residue consists in a phosphorylated serine residue, represents a great advantage over the known methods, not only because it is easier to be performed, but also because as will be illustrated in the non-limiting examples below, it represents a robust, meaningful, sensitive, and specific marker for the prediction of the probable outcome (prognosis) of ccRCC. Besides, the detection of P-Ser-STAT3 confirms the diagnosis of ccRCC.

A third aspect of the invention is the use of antibodies and/or fragments thereof for detecting the presence of the Signal transducer and activator of transcription 3 (STAT3), which comprises the amino acid sequence SEQ ID NO: 1 in an isolated sample of a subject for the diagnosis and/or prognosis of clear cell Renal Cell Carcinoma in any of the methods as disclosed above.

Another aspect of the invention is a method for determining the efficacy of a medical regimen in a patient already diagnosed of ccRCC, the method comprising the steps of:
(a) in vitro measuring the amount of P-Ser-STAT3 in a sample from the patient prior to the medical regimen:
(b) in vitro measuring the amount of P-Ser-STAT3 in a sample from the patient once started the medical regimen; and
(c) comparing the amounts measured in steps (a) and (b), in such a way that if the P-Ser-STAT3 amount measured in step (b) is different than the P-Ser-STAT3 amount measured in step (a), it is indicative that the medical regimen is effective in the treatment of ccRCC;
or, alternatively, the method comprising the steps of:
(i) in vitro measuring the amount of P-Ser-STAT3 in a sample from the patient once started the medical regimen; and
(ii) determining whether the amount measured in step (i) falls within a P-Ser-STAT3 concentration reference range obtained from a group of subjects which do not have ccRCC,
wherein, if the P-Ser-STAT3 amount measured in step (i) is within the P-Ser-STAT3 concentration reference range, it is indicative that the medical regimen is effective in the treatment of ccRCC.

Indeed, the efficacy of the method of treatment can be followed by the determination of P-Ser-STAT3 and comparing the value obtained with one known to be the corresponding to a health subject.

DETAILED DESCRIPTION OF THE INVENTION

Figure 1:
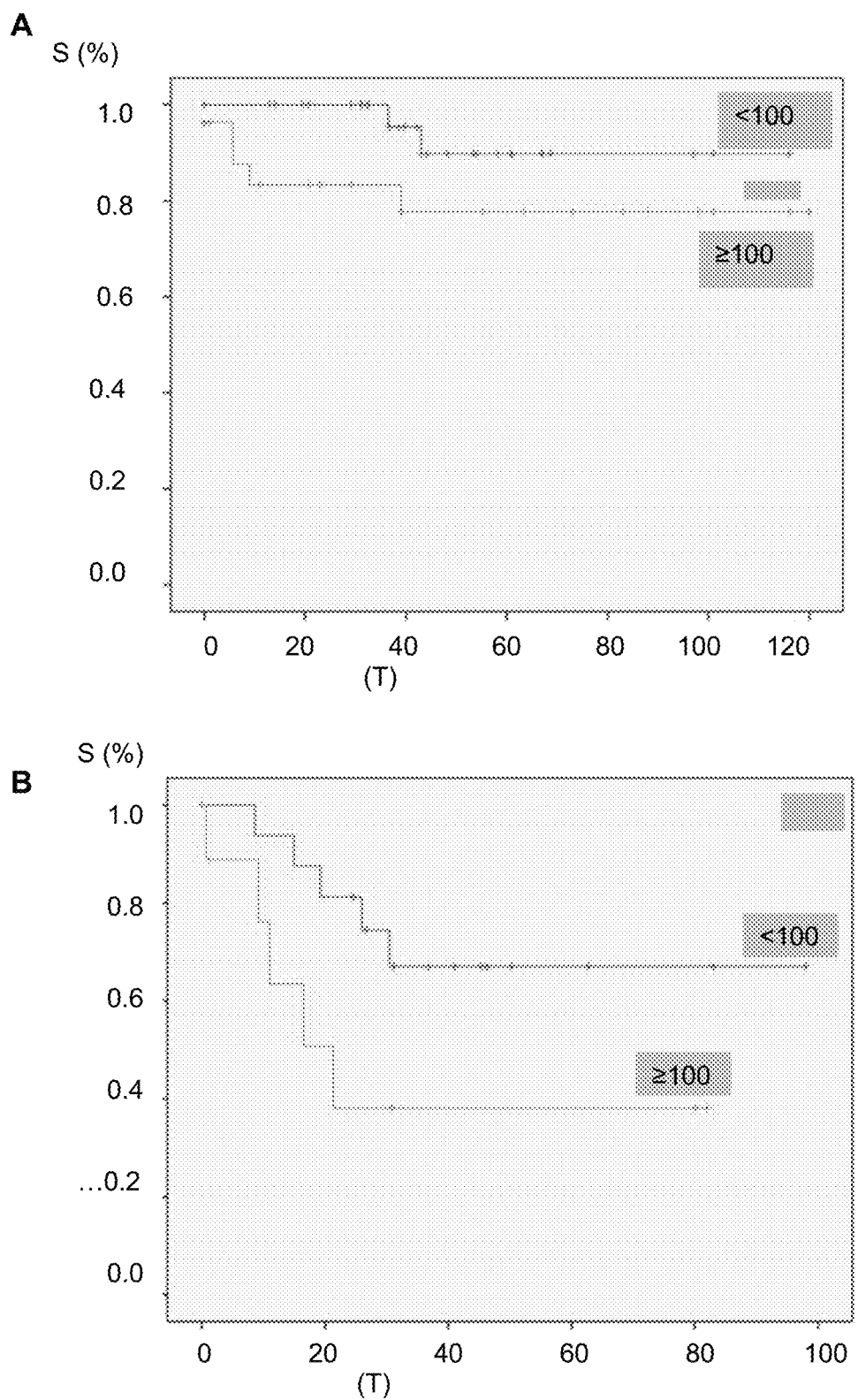
FIG. 1 shows the Kaplan Meier graphics, in which the percentage of survival (S %) of subjects suffering of ccRCC is evaluated along the time (T in months). Panel A shows data for subjects classified according to the Fuhrman gradation as Grade I or II. Panel (B) shows data for subjects classified according to the Fuhrman gradation as Grade III or IV. Line with <100 indicates the data for subjects in which the levels of P-Ser-STAT3 (SEQ ID NO: 2 with phosphorylation at residue Ser727) were lower than 100 measured in the biopsies according to HistoScore method (ImmuneHistoScore). Line with 100 indicates the data for subjects in which the levels of P-Ser-STAT3 (SEQ ID NO: 2 with phosphorylation at residue Ser727) were greater than 100 measured in the biopsies according to ImmuneHistoScore.

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition. The following definitions are included for the purpose of understanding.

The "Signal transducer and activator of transcription 3•also known as "STAT3" is a transcription factor which in humans is encoded by the STAT3 gene. The protein encoded by this gene is a member of the STAT protein family. In response to cytokines and growth factors, STAT family members are phosphorylated by receptor-associated kinases and then form homo- or heterodimers that translocate to the cell nucleus, where they act as transcription activators. This protein is activated through phosphorylation of tyrosine 705, in response to various cytokines and growth factors including interferons, epidermal growth factor, Interleukin 5, Interleukin-6, hepatocyte growth factor, leukemia inhibitory factor (LIF), bone morphogenetic protein 2 and also the hormone leptin. STAT3 mediates the expression of a variety of genes in response to cell stimuli, and thus plays a key role in many cellular processes such as cell growth and apoptosis.

The term "Signal transducer and activator of transcription 3 (STAT3)" includes the mammal protein or polypeptide with the transcription factor activity, or any variant thereof having said transcription factor activity. A "variant of STAT3 with transcription factor activity" refers to mutants of mammal STAT3 showing substantially the same activity of STAT3 or maintaining at least one of the functions of the wild-type STAT3 relating to transcription of nucleic acids. Suitable functional assays that can be used to assess whether a given polypeptide is a functionally equivalent variant of STAT3 are those assays based on the detection of an active transcriptional union between a target gene and the transcription factor STAT3. Examples of kits for performing these types of assays include the TransAM® STAT3 & STAT Family Kits of Active Motif. The variants include according to the present invention amino acid sequences being at least 60%, 70%, 80%, 90%, 95%, 96%, 97%, 98%, or 99% identical or similar to native mammal STAT3. The identity between two amino acid sequences is preferably determined by using the BLASTP algorithm disclosed in Altschul, S. F., et. al. "Gapped BLAST and PSI-BLAST: a new generation of proteína database search programms",

*Nucleic Acids Research*—1997, Vol. No. 25, pp.: 3389-3402, and NCBI http://wmv.ncbi.nlm.nih.gov/BLAST.

The "test sample" or "sample", used herewith interchangeable refers to a sample of bodily fluid or a fragment of a tissue obtained for the purpose of diagnosis, prognosis, or evaluation of a subject of interest, such as a patient. In certain embodiments, such a sample may be obtained for the purpose of determining the outcome of an ongoing condition or to determine whether a pharmacological treatment should be applied to a subject.

The term "diagnosis" is known to the person skilled in the art. Diagnosing is understood as becoming aware of a particular medical condition, disease, complication or risk.

The term "subject" used herein and according to the present invention relates to a healthy individual, an apparently healthy individual or particularly an individual suffering from a disease (patient). The patient can be both a male and a female individual; particularly the patient is suffering from a clear cell carcinoma, in particular clear cell Renal Cell Carcinoma.

An "antibody or fragment thereof specifically binding P-Ser-STAT3" is to be understood as any immunoglobulin or fragment of the same able to bind any antigen defined by the P-Ser-STAT3. It includes monoclonal and polyclonal antibodies. The term "fragment of an antibody" encompasses any part of an antibody having the size and conformation suitable to bind an epitope of P-Ser-STAT3. Suitable fragments include F(ab), F(ab') and Fv. An "epitope" is the part of the antigen being recognized by the immune system (B-cells, T-cells or antibodies). Suitable antibodies may be those mentioned in the examples, such as the rabbit polyclonal antibody of Cell Signalling (Cell signaling Ref 9134; http://www.cellsignal.com/products/9134.html).

In the present invention, the expression "medical regimen" is to be understood as encompassing either pharmacological therapies (such chemotherapy) as well as therapeutically surgical interventions (such as partial or total nephrectomy), as well as other clinical decisions taken by the oncologist concerning, for instance, hospitalization or discharge decisions, or dietary or social habits pointed by the doctor such as salt ingestion, liquid intake or physical activity.

The expression "reference value", which can be also understood as a "reference range" depending on the methodology employed for performing the measure of P-Ser-STAT3 or KIM-1 in the present invention, is to be understood as the control reference range or value in order to perform any of the methods of the present invention. The subjects (controls) selected to determine the reference value concentration or reference range are chosen on the basis of the requirement that such subjects do not have ccRCC. Control subjects can also be patients suffering from ccRCC, which are used in order to know the pathological stage of the test sample.

The expression "pathological level" or "pathological stage" or "pathological grade" or "pathological state" used herewith as synonymous refers to the stage of the cancer, generally determined by removing tissue samples (surgery, biopsy) and looking at how the cells look like under a microscope. Examples of tools for determining and analysing the pathological stage of a cancer include the Füuhrman gradation (or method), the Clinical Stage and the classification by the Group of Risk.

The invention provides a reliable in vitro method for the diagnosis and/or prognosis of clear cell Renal Cell Carcinoma, in which the Signal transducer and activator of transcription 3 (STAT3) which comprises the amino acid sequence SEQ ID NO:1 (DATNILVXPL), wherein X means a phosphorylated serine residue, is used as marker.

In a preferred embodiment the in vitro method further comprises the step of:
a) determining the levels of expression of the Signal transducer and activator of transcription 3 (STAT3) which comprises the amino acid sequence SEQ ID NO:1 (P-Ser-STAT3);
b) comparing the levels of P-Ser-STAT3 of step a) with a reference value; wherein if the levels of step a) are equal or higher than the reference value it is indicative of a bad prognosis, and
wherein if the levels of step a) are lower than the reference value it is indicative of a good prognosis.

In a preferred embodiment, the reference value of the levels of expression of P-Ser-STAT3 is 100, measured by the Immunohistochemistry method Histo-Score method, and calculated according to formula (I):

$$H\text{Score}=1\times(\% \text{ of cells with weak staining})+2\times(\% \text{ of cells with moderate staining})+3\times(\% \text{ of cells with strong staining}) \quad (I),$$

in which weak staining, moderate staining and strong staining are defined according to Detre S et al., A "quickscore" method for immunohistochemical semiquantitation: validation for estrogen receptor in breast carcinomas. *J Clin Pathol*—1995; Vol. No. 48, pp.: 876-878.

As a general mode, for Histo-score (H-score) assessment, a specified number of fields (generally 10) are random chosen a at a specified magnification (generally ×400) and the stain intensity in the malignant cell nuclei of a biopsy is scored as 0, 1, 1, 2, or 3 corresponding to the presence of negative, weak, intermediate-moderate, and strong staining, respectively. The total number of cells in each field and the number of cells stained at each intensity are counted. The average percentage positive is calculated applying the formula (I).

Indeed, the determination of the intensity of staining is well known by the facultative trained to analyse these kind of processed samples.

In another embodiment, the reference value of the levels of expression of P-Ser-STAT3 is a reference range comprised from 95 to 120, also measured by the Immunohistochemistry method Histo-Score method, and calculated according to formula (I). The reference range include the low and upper limit values, that is 95 and 120, as well as 100, 105, 110, and 115.

Other means for determining and measuring the amount of P-Ser-STAT3 in a sample include other immunohistochemistry methods in which the intensity of the staining is correlated with the malignancy of the tumour.

Other means not related with immunohistochemistry include specific DNA binding ELISAs, in which a target DNA for P-Ser-STAT3 is detected if a test sample includes P-Ser-STAT3, Western Blots and electrophoretic tools (2D-electrophoresis).

In another embodiment, the Signal transducer and activator of transcription 3 (STAT3) comprises the amino acid sequence SEQ ID NO: 2, which comprises a phosphorylated serine residue in the position 727.

SEQ ID NO: 2 corresponds to human STAT3 protein with the UniProtKB/Swiss-Prot Accession Number P40763, Version 138 of the entry of Jul. 11, 2012, and version 2 of the sequence of Jun. 7, 2004.

In a most preferred embodiment of the in vitro method, the Signal transducer and activator of transcription 3

(STAT3) consists in the amino acid sequence SEQ ID NO: 2, which comprises a phosphorylated serine residue in the position 727.

In another embodiment the Signal transducer and activator of transcription 3 (STAT3) comprises the amino acid sequence SEQ ID NO: 3, which comprises a phosphorylated serine residue in the position 727.

SEQ ID NO: 3 corresponds to mouse STAT3 protein with the UniProtKB/Swiss-Prot Accession Number P42227, Version 144 of the entry of Jul. 11, 2012, and version 2 of the sequence of Oct. 1, 1996.

All those mammalian STAT3 and/or fragments thereof, which have substantially the same biological activities, can also be used in the methods of the invention.

Indeed, SEQ ID NO: 1 is not only maintained between mammals, but also other species such as ayes (e.g.: *Gallus*) and amphibian (e.g.: *Xenophus*) have STAT3 proteins with SEQ ID NO: 1 (DATNILVXPL). Thus, in case the serine is phosphorylated and a ccRCC can be diagnosed, a bad prognosis is to be expected in all these animals.

In another embodiment, the isolated sample of the subject is selected from the group consisting of a renal tissue biopsy, and a biofluid selected in turn from the group consisting of whole blood, blood serum, plasma, urine, saliva, and from cells from urine. Indeed, cells from urine include renal cells that due to detaching or scaling from the urinary system.

In a most preferred embodiment the isolated sample is a renal tissue biopsy. In a particular embodiment, the renal tissue biopsy is from a renal neoplasm (tumour), which has been excised from a subject.

In another preferred embodiment, the detection of the presence of P-Ser-STAT3, that is, a STAT3 protein which comprises the amino acid sequence SEQ ID NO:1 (DATNILVXPL), wherein X means a phosphorylated serine residue, is carried out by means of specific antibodies and/or fragments thereof, said antibodies and/or fragments specifically recognizing the serine-phosphorylated residue.

Yet in another preferred embodiment, the method further comprises the steps of:
a) measuring in an isolated sample test of the subject the presence and the amount of the mammalian protein Kidney Injury Molecule-1 (KIM-1); and
b) determining whether the amount of step a) is higher than a reference value, wherein if the levels of KIM-1 are higher than said reference value, it is indicative of ccRCC and of bad prognosis.

As will be depicted in the examples below, the presence of this protein is also a good marker not only for corroborating the diagnosis of the diseases, but also to predict the most probable progression of the same (bad prognosis or good prognosis).

This tool taken in combination with the determination of P-Ser-STAT3 gives a powerful information to the facultative, who is facing a ccRCC case.

In humans KIM-1 protein corresponds to UniProtKB/Swiss-Prot Accession Number Q96D42, Version 93 of the entry of Jun. 13, 2012, and version 2 of the sequence of Aug. 30, 2005. This protein is also known as Hepatitis A virus cellular receptor 1 (HAVCR). The protein has a length of 359 amino acids. KIM-1 is a transmembrane protein codified in human in chromosome 5 (Cr 5q). The ectodomain of KIM-1 is delivered to the systemic circulation by means of metalloproteases.

In mice, KIM-1 protein corresponds to UniProtKB/Swiss-Prot Accession Number Q5QNS5, Version 67 of the entry of Jul. 11, 2012, and version 2 of the sequence of Aug. 30, 2005. This protein is also known as Hepatitis A virus cellular receptor 1 homolog. The protein isoform 1 has 305 amino acids. There are two isoforms in mice produced by alternative splicing. Isoform 2 differs from the canonical sequence of isoform 1 in that amino acids 183-205 are missing.

It is known in the art that extracellular domain of KIM-1 may be detected in urine of patients suffering from renal cancer, but the method is not specific enough to diagnose the cancer type. Nonetheless, HAVCR/KIM-1 has been found to be a sensitive and specific biomarker in identifying kidney injury and major types of kidney tumors, including papillary and the most common and aggressive type, the clear cell type (ccRCC). It seems likely that urine HAVCR/KIM-1 measurements together with routine blood marker for renal failure (creatinine) should distinguish kidney tumors from non-tumor kidney injury, therefore providing with a simple non-invasive method to screen patients for potential kidney tumors.

Document Lin et al. "Human Kidney Injury Molecule-1 (hKIM-1): A useful Immunohistochemical Marker for Diagnosing Renal Cell Carcinoma and Ovarian Clear Cell Carcinoma, *Am J Surg Pathol*—2007; 31:371-381, provides immunohystochemistry data of ccRCC biopsies, in which high levels of KIM-1 protein were detected in the tumours and even in peripheral areas of tumours. Also the document Sangoi et al., "Immunohistochemical Distinction of Primary Adrenal Cortical Lesions From Metastatic Clear Cell Renal Cell Carcinoma: A Study of 248 Cases", de *Am J Surg Pathol*—2011, Vol No. 35(5), shows an assay with a great number of patients, some of them suffering from ccRCC, in which the staining of the tissue indicates a diffuse distribution of the protein between the membrane and the cytosol.

In another preferred embodiment, the presence and the amount of the mammalian protein Kidney Injury Molecule-1 (KIM-1) is measured in the cytosol and the membrane of the cells of an isolated renal biopsy, and the expression distribution pattern of the protein is established, in such a way that if the expression distribution pattern shows a higher presence in the cytosol in relation to the membrane presence, it is indicative of ccRCC and of bad prognosis.

The expression distribution pattern of KIM-1 may be assessed by several means such as by immunohistochemistry means, membrane/cytosol fractionation and western blot assays. When immunohistochemistry is used, staining of the cytosol and of the membrane is determined. If the expression distribution pattern shows a higher staining in the cytosol in relation to the membrane staining, it is indicative of ccRCC and of bad prognosis.

The correlation of the bad prognosis and this expression distribution pattern of KIM-1 (majority in the cytosol than membrane in cases of ccRCC with an advanced pathological level or state) is provided for the first time.

Without being bound to theory, the inventors propose that malign tumours probably liberate the ectodomain of KIM-1 faster than the tumours in a less aggressive pathological stage. This hypothesis derives from the immunohystochemical analysis of the inventors from different tumours in different Fuhrman grades (see below).

In another embodiment, the isolated sample of the subject for measuring the amount of the mammalian protein Kidney Injury Molecule-1 (KIM-1) is urine. Although data not shown below, the inventors determined that in ccRCC patients, HAVCR/KIM-1 levels in urine correlated with tumor grade (Fuhrman grade) and HAVCR/KIM-1 shedding capacity (liberation of ectodomain) in vitro correlated with invasiveness. This would reinforce the value of HAVCR/KIM-1 as a non-invasive biomarker not only for ccRCC diagnosis but also for prognosis.

As above exposed, the invention also aims a method of deciding or recommending whether to initiate a medical regimen of a subject suspected of suffering clear cell Renal Cell Carcinoma, in which method if the presence of the P-Ser-STAT3 is detected in an isolated sample of a subject, a bad prognosis of clear cell Renal Cell Carcinoma is established; and then different interventions or regimens are recommended or applied in function of the pathological stage (gravity of the disease).

In a preferred embodiment of this method of deciding or recommending whether to initiate a medical regimen, the isolated sample is selected from the group consisting of renal tissue biopsy, a whole blood, blood serum, plasma, urine, saliva, and cells from urine. In another preferred embodiment the isolated sample is a renal tissue biopsy. In a particular embodiment, the renal tissue biopsy is from a renal neoplasm (tumour), which has been excised from a subject.

In another preferred embodiment, the method of deciding or recommending whether to initiate a medical regimen, further comprises the steps of:
a) measuring in an isolated sample test of the subject the presence and the amount of the mammalian protein Kidney Injury Molecule-1 (KIM-1),
b) determining whether the amount of step a) is higher than a reference value or reference range,
wherein if the levels of KIM-1 are higher than said reference value or range, it is indicative of ccRCC and of bad prognosis, and the patient (subject) is recommended for the suitable regime.

In another preferred embodiment of the method of deciding or recommending whether to initiate a medical regimen, the amount of the mammalian protein Kidney Injury Molecule-1 (KIM-1) is measured in the cytosol and membrane of the cells of a kidney biopsy; and the expression distribution pattern of KIM-1 is determined, wherein if the expression distribution pattern shows a higher presence in the cytosol in relation to the membrane presence, it is indicative of ccRCC and of bad prognosis and the subject is recommended for a partial or total nephrectomy.

There exist in the art antibodies or fragments thereof, specifically directed to the epitope in the Signal transducer and activator of transcription 3 (STAT3) that comprises the amino acid sequence SEQ ID NO:1 (DATNILVXPL), wherein X means a phosphorylated serine residue. These antibodies or fragments distinctively detect phosphorylated STAT3 from non-phosphorylated STAT3. All of them may be used in the methods disclosed above. Examples of these antibodies include, among others: Active Motif Catalog No: 39613, 39614, Cell Signalling Phospho-Stat3 (Ser727) Antibody #9134, GenScript A00251-100 STAT3 Antibody (Phospho-Ser$^{727}$).

In a preferred embodiment, said antibodies or fragments thereof form part of a kit. The kit may additionally comprise the means (additives, solvents) to visualize the antigen-antibody interactions (dipsticks, chemiluminescent reagents, turbidimetric reagents, etc.). Suitable additives, solvents and reagents to visualize the antigen-antibody interaction are disclosed in the examples. In a preferred embodiment, the kit is for performing a Western blot analysis. Western blot analysis requires not only the use of specific antibodies, but also the reagents for making an electrophoresis gel, the membranes for the transfer of the proteins submitted to electrophoresis (generally membranes of nitrocellulose or polyvinylidene difluoride (PVDF)), as well as any buffers or solutions to perform the protein immunobloting.

The means used for detecting the presence of P-Ser-STAT3 for the purpose of the invention may also be components or reagents of different commercial kits, or the means may be the combination of an antibody or of antibodies with reagents of other kits, for example to visualize the antigen-antibody interaction.

Other commercial kits that can be used for the detection of P-Ser-STAT3 inlcude, for example DNA binding Elisa kits, such as the TransAM® STAT3 & STAT Family Kits of Active Motif.

There are also antibodies or fragments thereof, which specifically bind several epitopes of the protein KIM-1. In a preferred embodiment, these antibodies or fragments thereof that specifically bind mammalian KIM-1, may be used in the methods disclosed above, for diagnosing and/or prognosing ccRCC.

Examples of anti-KIM-1 antibodies include, among others, Novus Biological NBP1-51251, TIM-1/KIM-1/HAVCR (R&D Systems, MAB1750). Said antibodies or fragments thereof may form part of a kit, which additionally comprises the means (additives, solvents) to visualize the antigen-antibody interactions (dipsticks, chemiluminescent reagents, turbidimetric reagents, etc.). In the alternative, the antibodies raised against epitopes of the protein KIM-1 may be components or reagents of different commercial kits.

As will be derived from the non-limitative examples below, the invention provides the use of a mammalian (including a human) Signal transducer and activator of transcription 3 (STAT3), which comprises the amino acid sequence SEQ ID NO:1 (DATNILVXPL), in which X means a phosphorylated serine residue, as clinical diagnostic and/or prognostic marker of ccRCC.

In a preferred embodiment, the Signal transducer and activator of transcription 3 (STAT3), which comprises the amino acid sequence SEQ ID NO:1 is a clinical prognosis marker in a renal tissue biopsy.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Data from the examples below come from the analysis of clinical and pathological incomes of 168 patients with treated renal tumours (partial or radical-total nephrectomy) in Hospital Vall d'Hebron and under the consent of the patients. The disposable information included diagnostic conclusions, demographic information, clinical stage, Fuhrman grade, Risk factor, etc. of 98 patients with ccRCC.

Example 1

P-Ser-STAT3 as Diagnostic and Prognostic Marker of ccRCC

Biopsies of the 98 patients with ccRCC were analysed to detect the presence of P-Ser-STAT3 (SEQ ID NO: 2 with the phosphorylated residue Ser 727).

Using immunohistochemistry tools, different antigens may be detected in the samples (tissular sections of renal tumours, ccRCC). The samples were fixed in formaldehyde, paraffin embedded and cut to sections of 5 µm according to the following protocol:

Each sample was incubated with the primary antibody after the excess of paraffin was eliminated and the tissue cut washed with the phosphate buffer saline-triton buffer (PBS-T). For the detection of P-Ser-STAT3 the rabbit polyclonal antibody pSTAT3S (Cell signaling Ref 9134.) from Cell Signaling was used at a dilution of 1:1000, at room temperature (r.t.) for 1 hour. Then, the antigen-antibody interaction was detected with a secondary antibody system (Dako real EnVision HRP Rabbit/Mouse). The appropriate EnVision detection system (Dako, Carpinteria, Calif.) and 3,3'-diaminobenzidine as chromogen were used and the slides counterstained with hematoxylin. As a negative control, the primary antibody was replaced with a non-immune mouse serum. TMA sections were scored by two independent pathologists. Discrepancies were resolved by a concurrent re-examination by both researchers using a double-headed microscope. The expression of the target (P-Ser-STAT3) antigen was evaluated in a semiquantitative manner by the ImmuneHistoScore methodology (H-Score) based on the percentage of stained epithelial cells, and intensity of staining was calculated. The intensity score was defined as: 0=no appreciable staining in cells; 1=weak-intensity cells; 2=intermediate intensity of staining; and 3=strong intensity of staining. [H-Score=1×(% weak)+2×(% moderate)+3×(% intense) ranging from 0 to 300]. A mean of three cores was obtained for each case. This scoring was used for the statistical analysis.

After the immunohistochemistry analysis of the samples, P-Ser-STAT3 was revealed as an important molecule for the follow-on in ccRCC. In FIG. 1 it is depicted the percentage of survival (S %) of subjects suffering of ccRCC along the time (T in months). Using the Kaplan Meier graphics, Panel A shows data for subjects classified according to the Fuhrman gradation as Grade I or II, and Panel B shows data for subjects classified according to the Fuhrman gradation as Grade III or IV. Line with <100 indicates the data for subjects in which the levels of P-Ser-STAT3 (SEQ ID NO: 2 with phosphorylation at residue Ser727) were lower than 100 measured in the biopsies according to HistoScore. Line with 100 indicates the data for subjects in which the levels of P-Ser-STAT3 (SEQ ID NO: 2 with phosphorylation at residue Ser727) were greater than 100 measured in the biopsies according to ImmuneHistoScore.

According to the Fuhrman grade classification of the patients, the levels of expression of P-Ser-STAT3 allows distinguishing between different survival percentages in function of the developing of the disease. Thus, patients with Fuhrman grades I-II had a survival mean of 108 months (standard confidence level of 95%) when the expression of the marker measured using HistoScore method was lower than 100. For those patients with expression levels of P-Ser-STAT3 equal or greater than 100, the survival mean was of 96 months (p<0.02).

In the same way, those patients catalogued with Fuhrman grades III-IV, the survival mean was of 72 months when the expression of the marker measured using HistoScore method was lower than 100, and it was reduced to 38 months when the expression levels of P-Ser-STAT3 was equal or greater than 100 (p<0.01).

Similar results were obtained evaluating the patients according to the Risk Group or the Clinical Stage.

These results indicate that survival levels (indicated in FIG. 1 as (:)/0 of survival) of patients with ccRCC are drastically reduced when P-Ser-STAT3 is present in the samples and at levels greater or equal to 100 (reference value). Thus, the molecule can be considered a valuable prognostic marker of the disease independently of the pathological grade of the patient, the group of risk and the pathological or clinical state. In all the levels of the patient classification with ccRCC, survival of the patient is really compromised and reduced, with a high statistically meaning, independently of the patient grouping, when the levels of the molecule are high.

Following Table 1 shows shows the specific-cancer survival for each grouping in relation with the levels of P-Ser-STAT3 detected in the samples.

TABLE 1

| P-Ser-STAT3 HistoScore expression level | | Mean survival (months) (95% CI) | p-value |
|---|---|---|---|
| Führman grade I-II | <100 | 108 (98-118) | p < 0.02 |
| | >100 | 96 (78-114) | |
| Führman grade III-IV | <100 | 72 (54-91) | p < 0.01 |
| | >100 | 38 (15-62) | |
| Clinical stage I-II (Tumour size cathegory 1 or 2, no nodules no metastasis (pT1-2N0M0)) | <100 | 106 (95-116) | p < 0.003 |
| | >100 | 92 (73-111) | |
| Clinical stage III-IV (Tumour size cathegory 3 or 4, nodules and metastasis (pT3-4 N0-1M0-1)) | <100 | 76 (58-94) | p < 0.001 |
| | >100 | 19 (0.4-38) | |
| Low Risk | <100 | 106 (96-116) | p < 0.001 |
| | >100 | 98 (95-114) | |
| High Risk | <100 | 72 (52-93) | p < 0.001 |
| | >100 | 17 (32-68) | |

For establishing the Clinical Stage it was determined in the biopsies the size of the tumour (then categorized from 1 to 4), the presence of nodules near the tumour and the presence or absence of metastasis.

When patients were classified according to the Clinical Stage, those which were in Clinical Stages I or II and a P-Ser-STAT3 lower than 100, behave a survival of 106 months, whereas if values of P-Ser-STAT3 were over 100, survival was reduced to 92 months (reduction of 20% of survival rate measured at 40 months of follow up). On the other hand, those patients of Clinical Stages III and IV, survival was of 76 months if P-Ser-STAT3 was lower than 100, and of 19 months (reduction of 80% of survival rate measured at 40 months of follow up) when P-Ser-STAT3 was higher than 100.

When patients were classified according to Risk Group, multiple variables per patients were determined which are considered according to the clinical practice as parameters involved in the progression of this type of cancer (advanced age, sex, habits, etc.). The group of Low Risk have a survival rate of 106 months if P-Ser-STAT3 was lower than 100, and of 98 months when P-Ser-STAT3 was higher than 100. If the patients were categorized as of High Risk, a survival rate of 72 months if P-Ser-STAT3 was lower than 100, and of 17 months when P-Ser-STAT3 was higher than 100 (this represented a reduction of 80% of survival rate measured at 40 months of follow up).

Example 2

Expression Distribution Pattern of the Protein KIM-1 in Patients with ccRCC

Also with the samples of the 98 patients with ccRCC, an immunohistochemistry assay was performed to evaluate the expression of KIM-1.

Four-μm sections of a tumor tissue microarray (TMA) block were obtained and transferred to glass slides. Tissue was deparaffinized and an immunoperoxidase staining system was used for immunohistochemistry analysis. Antigens were retrieved through treatment with 10 mM sodium citrate, pH 6.0, in a 95° C. water bath for 20 min. Endogenous peroxidases were blocked with 3% hydrogen peroxide for 10 min, proteins were blocked with 5% normal horse serum for 30 min and endogenous biotin was blocked with an avidin-biotin kit for 20 min.

Sections were then incubated for 1 h at room temperature with monoclonal murine anti-human KIM-1 antibody at a final concentration of 0.1 μg/ml. The appropriate EnVision detection system (Dako, Carpinteria, Calif.) and 3,3'-diaminobenzidine as chromogen were used and the slides counterstained with hematoxylin. As a negative control, the primary antibody was replaced with a non-immune mouse serum. TMA sections were scored by two independent pathologists. Discrepancies were resolved by a concurrent re-examination by both researchers using a double-headed microscope. The expression of the target antigen was evaluated in a semiquantitative manner by the ImmuneHistoScore methodology (H-Score) based on the percentage of stained epithelial cells, and intensity of staining was calculated. Cytosol, membrane and total KIM-1 expression was evaluated on each sample. The intensity score was defined as: 0=no appreciable staining in cells; 1=weak-intensity cells; 2=intermediate intensity of staining; and 3=strong intensity of staining. [H-Score=1×(% weak)+2×(% moderate)+3×(% intense) ranging from 0 to 300]. A mean of three cores was obtained for each case. This scoring was used for the statistical analysis.

Each sample was analysed in triplicate and the mean of the punctuation was recorded.

Analysis, not shown, of total staining of KIM-1 revealed no meaningful association with any of the anatomic-pathologic parameters under study, including the clinical stage of the disease, the Fuhrman grade and the Group of Risk classification.

However, it was observed a specific pattern of distribution of the expressed (translated) protein between the membrane and the cytosol of the cells in the samples.

Figure 2:
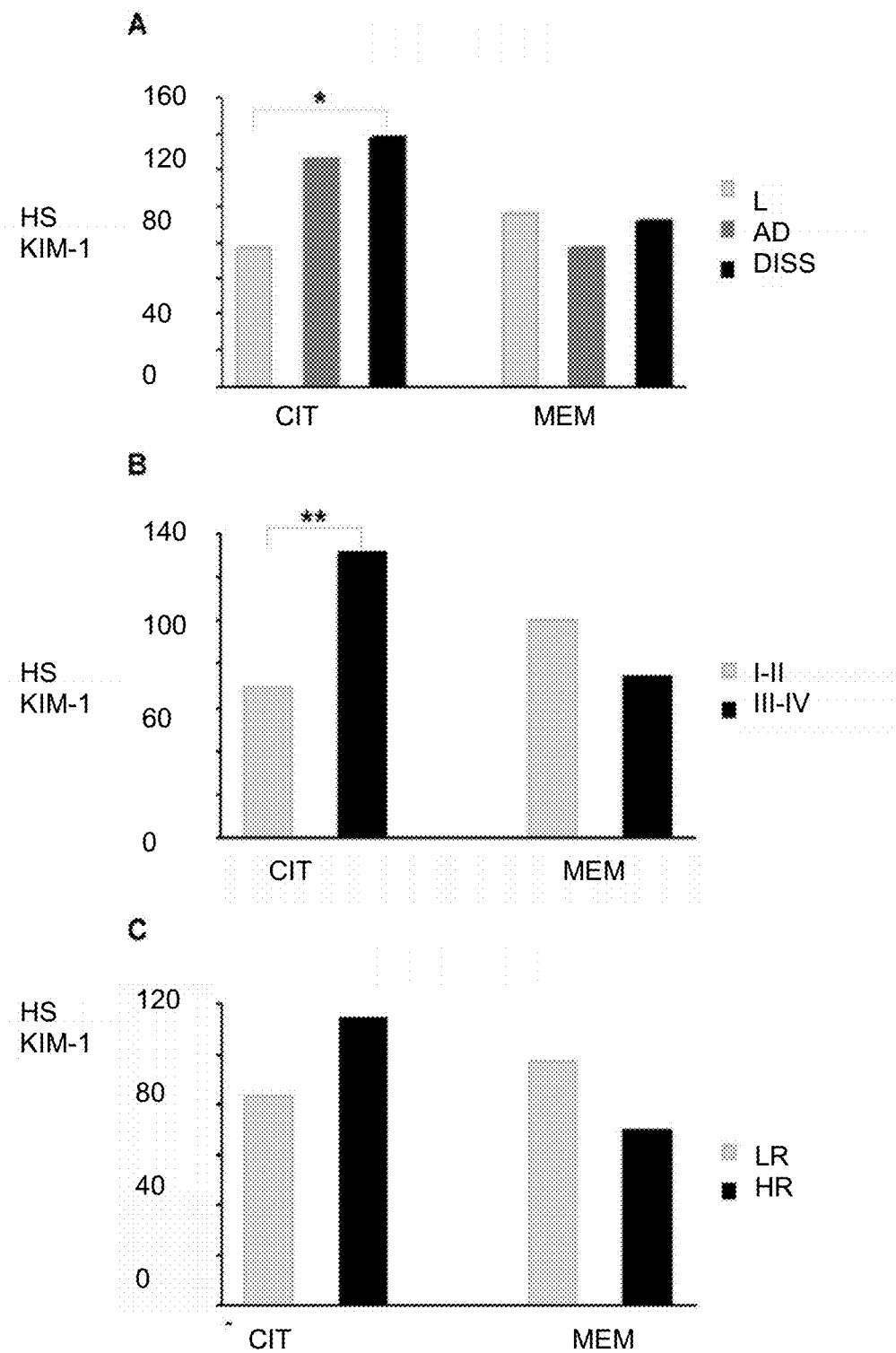
FIG. 2 is a bar diagram showing the ImmuneHistoScore value of KIM-1 expression (HS KIM-1) in 98 subjects suffering from ccRCC in the cytosol (CIT) and the membrane (MEM) of the biopsies. Patients (subjects) are grouped according to the clinical stage (panel A), the Fuhrman grade (Panel B) and the Risk group (Panel C) to which they were previously catalogued. In panel A, L means localized (light grey bars), AD means advanced (dark grey bars), and DISS means disseminated tumour (black bars). In panel B, I-II means Fuhrman grades I and II, and III-IV means Fuhrman grades III and IV. In panel C, LR means low risk, and HR means high risk.

As can be seen in FIG. 2, all those tumours classified as disseminate tumours or of elevated grade according to Fuhrman gradation, or of high risk comprise higher levels of the protein KIM-1 in the cytosol than in the membrane of the cells.

This FIG. 2 is a bar diagram showing the ImmuneHistoScore value of KIM-1 expression (HS KIM-1) in the cytosol (CIT) and the membrane (MEM) of the cells of the biopsies of those 98 subjects suffering from ccRCC. Patients (subjects) are grouped according to the clinical stage (panel A), the Fuhrman grade (Panel B) and the Risk group (Panel C) to which they were previously catalogued.

In addition, according to the Fuhrman gradation, the expression distribution pattern (cytosol/membrane) is different in patients with grade III-IV in respect of the lower grades I-II.

All these examples allow concluding that mammalian Signal transducer and activator of transcription 3 (STAT3), which comprises the amino acid sequence SEQ ID NO:1 (DATNILXSPL), in which X means a phosphorylated serine residue, in particular the human STAT3 of SEQ ID NO: 2, which at residue 727 has a phosphorylated serine, is a good biomarker for determining the prognosis of clear cell Renal Cell Carcinoma.

In addition, the analysis of the expression distribution pattern of the human protein KIM-1 provides important information also with regard to the state of the disease.

Both parameters are envisaged as powerful tools in the clinical diagnosis and prognosis of renal cancers. In particular, they represent interesting means for rapidly detecting one of the most prevalent and malignant renal cancers, ccRCC.

In parallel to all these experimental observations, the inventors also studied the signal transduction pathway in the samples of the patients. Using also the method of HistoScore they observed the activation of JAK-STAT pathway.

Apart from the antibodies used for the detection of P-Ser-STAT3, there were used antibodies raised against interleukin-6 (IL-6) and against an epitope of STAT3 including the tyrosine residue at position 705 of the human protein sequence (SEQ ID NO: 2). The inventors observed a cytoplasmic staining in normal tissue that turned to major nuclear staining in tumour samples.

All these data as a whole revealed not only that this pathway is activated in this kind of cancer, but also that P-Ser-STAT 3 was the final target, which can be used as an independent prognostic marker for the disease.

REFERENCES CITED IN THE APPLICATION

Guo et al., "Activation of STAT3 in renal tumors", *Am. J. Transl Res*—2009, vol. 1(3), pp.: 283-290.

Horiguchi et al., "Activation of signal transducer and activator of transcription 3 in renal cell carcinoma: A study of incidence and its association with pathological features and clinical outcome", The Journal of Urology—2002, Vol. 168, pp. 762-765.

Komohara et al. "Macrophage infiltration and its prognostic relevance in clear cell renal cell carcinoma", Japanese Cancer Association—2011, Vol. 102(4), pp.: 1424-1431.

Dong et al., "Expression and clinical significance of Kidney Injury Molecule 1 in renal epithelial neoplasms, PUBMED 20368397, Zhonguabing-2010,Vol. 39(1), pp. 35-39.

Dudka et al., "STAT3 BINDING TO THE FGF RECEPTOR IS ACTIVATED BY RECEPTOR AMPLIFICATION", *Cancer Res.*—2010, Vol. No. 70(8), pp.: 3391-3401.

Hazan-Halevy et al., "STAT3 is constitutively phosphorylated on serine 727 residues, binds DNA, and activates transcription in CLL cells", *Blood*—2010 vol. 115 (14), pp.: 2852-2863.

Vacas et al., "Vasoactive Intestinal Peptide (VIP) inhibits human renal cell carcinoma proliferation", Biochimica et Biophysica Acta—2012, Vol 1823, pp.: 1676-1685.

Lin et al. "Human Kidney Injury Molecule-1 (hKIM-1): A useful Immunohistochemical Marker for Diagnosing Renal Cell Carcinoma and Ovarian Clear Cell Carcinoma, *Am J Surg Pathol*—2007; 31:371-381.

Sangoi et al., "Immunohistochemical Distinction of Primary Adrenal Cortical Lesions From Metastatic Clear Cell Renal Cell Carcinoma: A Study of 248 Cases", de *Am J Surg Pathol*—2011, Vol No. 35(5).

E. Oosterwdk, et al., "Monoclonal antibody G 250 recognizes a determinant present in renal-cell carcinoma and absent from normal kidney", *Int Journal of Cancer*—1986, Vol. No. 38; pp. 489-494

Altschul, S. F., et. al. "Gapped BLAST and PSI-BLAST: a new generation of proteína database search programms", *Nucleic Acids Research*—1997, Vol. No. 25, pp.: 3389-3402.

Detre S et al., A "quickscore" method for immunohistochemical semiquantitation: validation for estrogen receptor in breast carcinomas. *J Clin Pathol*—1995; Vol. No. 48, pp.: 876-878.

The invention claimed is:

1. A method for determining a prognosis and treatment of clear cell carcinoma in a subject diagnosed with the disease, said method comprising the steps of:
   a) obtaining a first sample comprising a renal tissue biopsy sample or a urine sample from the subject;
   b) contacting the first sample with a first reagent that binds to the phosphorylated serine residue at position 727 of a signal transducer and activator of transcription 3 (STAT3) protein encoded by SEQ ID NO: 2;
   c) measuring an amount of protein that is bound to the first reagent in the first sample;
   d) comparing the amount of protein bound to the first reagent in step c) with a STAT3 reference value;
   e) determining the prognosis for the subject and treating the subject, wherein:
      (i) if the amount of protein bound to the first reagent in step c) is equal to or greater than the STAT3 reference value, the prognosis is poor, and the treatment comprises surgical intervention comprising a partial or total nephrectomy; and
      (ii) if the amount of protein bound to the first reagent in step c) is less than the STAT3 reference value, the prognosis is good, and the treatment is selected from the group consisting of: partial nephrectomy, follow-up, chemotherapy, and combinations thereof;
   wherein poor prognosis is understood to indicate a mean survival period of 96 months in Führman grades I and II determination of the pathological state and a mean survival period of 38 months in Führman grades III and IV determination of the pathological state; and
   wherein good prognosis is understood to indicate a mean survival period of 108 months in Führman grades I and II determination of the pathological state and a mean survival period of 72 months in Führman grades III and IV determination of the pathological state.

2. The method according to claim 1, wherein the clear cell carcinoma is clear cell renal cell carcinoma (ccRCC).

3. The method according to claim 1, wherein the STAT3 reference value is 100, measured by an immunohistochemistry Histo-Score method (H-score), and calculated according to formula (I):

$$\text{HScore} = 1\times(\% \text{ of cells with weak staining}) + 2\times(\% \text{ of cells with moderate staining}) + 3\times(\% \text{ of cells with strong staining}) \quad \text{(formula I)}.$$

4. The method according to claim 1, wherein the first sample is a renal tissue biopsy.

5. The method according to claim 1, wherein the first reagent is an antibody or antibody fragment that specifically recognizes the phosphorylated serine residue at position 727 of SEQ ID NO: 2.

6. The method according to claim 1, further comprising the steps of:
   d1) obtaining a second sample from the subject;
   d2) contacting the second sample with a second reagent that binds to mammalian protein kidney injury molecule-1 (KIM-1);
   d3) measuring the amount of KIM-1 bound to the second reagent in the second sample; and
   d4) comparing the amount of KIM-1 bound to the second reagent in step d3) to a KIM-1 reference value,
   wherein if the amount of KIM-1 bound to the second reagent is greater than said KIM-1 reference value, the result indicates a poor prognosis for the subject.

7. The method according to claim 6, wherein the presence and the amount of KIM-1 is measured in a group of cells of an isolated renal biopsy to establish a distribution pattern between the amount of KIM-1 in the cytosol of the cells and the amount of KIM-1 in the membrane of the cells, and wherein if the expression distribution pattern shows a higher amount of KIM-1 in the cytosol in relation to the amount of KIM-1 in the membrane, the result indicates a poor prognosis for the subject.

8. A method for treating clear cell carcinoma in a subject suffering from clear cell carcinoma, wherein the method comprises the steps of:

a) obtaining a sample from the subject, wherein the sample is selected from the group consisting of: a renal tissue biopsy, urine, and cells from urine;
b) contacting the sample from the subject with a reagent that binds to a signal transducer and activator of transcription 3 (STAT3) protein comprising SEQ ID NO: 2, wherein the reagent binds at the phosphorylated serine residue at position 727 of SEQ ID NO: 2;
c) measuring an amount of STAT3 protein bound to the reagent in the sample;
d) comparing the amount of STAT3 protein bound to the reagent in step c) with a reference STAT3 value; and
e) treating the subject, wherein:
   (i) if the amount of STAT3 protein bound to the reagent in step c) is equal to or greater than the reference STAT3 value, the treatment comprises a surgical intervention comprising a partial or total nephrectomy; and
   (ii) if the amount of STAT3 protein bound to the reagent in step c) is less than the reference STAT3 value, the treatment is selected from the group consisting of: partial nephrectomy, follow-up, chemotherapy, and combinations thereof.

9. The method of claim 8, wherein the sample is a renal tissue biopsy.

10. The method according to claim 5, wherein the antibody or antibody fragment is provided in a kit.

11. The method according to claim 6, wherein the second sample is selected from the group consisting of renal tissue biopsy, urine, and cells from urine.

12. The method according to claim 8, wherein the clear cell carcinoma is clear cell renal carcinoma (ccRCC).

13. The method according to claim 11, wherein the second sample is a renal tissue biopsy.

\* \* \* \* \*

SEQUENCE LISTING

```
<160> NUMBER OF SEQ ID NOS: 3

<210> SEQ ID NO 1
<211> LENGTH: 10
<212> TYPE: PRT
<213> ORGANISM: Homo sapiens
<220> FEATURE:
<221> NAME/KEY: PHOSPHORYLATION
<222> LOCATION: (8)..(8)
<223> OTHER INFORMATION: Phosphorylated Serine

<400> SEQUENCE: 1

Asp Ala Thr Asn Ile Leu Val Xaa Pro Leu
1               5                   10

<210> SEQ ID NO 2
<211> LENGTH: 770
<212> TYPE: PRT
<213> ORGANISM: Homo sapiens
<220> FEATURE:
<221> NAME/KEY: MOD_RES
<222> LOCATION: (727)..(727)
<223> OTHER INFORMATION: PHOSPHORYLATION

<400> SEQUENCE: 2

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
            35                  40                  45

Lys Glu Ser His Ala Thr Leu Val Phe His Asn Leu Leu Gly Glu Ile
        50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205
```

```
Ala Leu Asp Gln Met Arg Arg Ser Ile Val Ser Glu Leu Ala Gly Leu
210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
            420                 425                 430
Thr Glu Glu Leu His Leu Ile Thr Phe Glu Thr Glu Val Tyr His Gln
        435                 440                 445
Gly Leu Lys Ile Asp Leu Glu Thr His Ser Leu Pro Val Val Val Ile
450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                485                 490                 495
Pro Ile Gly Thr Trp Asp Gln Val Ala Glu Val Leu Ser Trp Gln Phe
            500                 505                 510
Ser Ser Thr Thr Lys Arg Gly Leu Ser Ile Glu Gln Leu Thr Thr Leu
        515                 520                 525
Ala Glu Lys Leu Leu Gly Pro Gly Val Asn Tyr Ser Gly Cys Gln Ile
530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
            580                 585                 590
Arg Glu Arg Ala Ile Leu Ser Thr Lys Pro Pro Gly Thr Phe Leu Leu
        595                 600                 605
Arg Phe Ser Glu Ser Ser Lys Glu Gly Gly Val Thr Phe Thr Trp Val
610                 615                 620
Glu Lys Asp Ile Ser Gly Lys Thr Gln Ile Gln Ser Val Glu Pro Tyr
```

```
                625                 630                 635                 640
        Thr Lys Gln Gln Leu Asn Asn Met Ser Phe Ala Glu Ile Ile Met Gly
                        645                 650                 655

Tyr Lys Ile Met Asp Ala Thr Asn Ile Leu Val Ser Pro Leu Val Tyr
                        660                 665                 670

Leu Tyr Pro Asp Ile Pro Lys Glu Glu Ala Phe Gly Lys Tyr Cys Arg
                        675                 680                 685

Pro Glu Ser Gln Glu His Pro Glu Ala Asp Pro Gly Ser Ala Ala Pro
                        690                 695                 700

Tyr Leu Lys Thr Lys Phe Ile Cys Val Thr Pro Thr Thr Cys Ser Asn
        705                 710                 715                 720

Thr Ile Asp Leu Pro Met Ser Pro Arg Thr Leu Asp Ser Leu Met Gln
                        725                 730                 735

Phe Gly Asn Asn Gly Glu Gly Ala Glu Pro Ser Ala Gly Gly Gln Phe
                        740                 745                 750

Glu Ser Leu Thr Phe Asp Met Glu Leu Thr Ser Glu Cys Ala Thr Ser
                        755                 760                 765

Pro Met
            770

<210> SEQ ID NO 3
<211> LENGTH: 770
<212> TYPE: PRT
<213> ORGANISM: Mus musculus
<220> FEATURE:
<221> NAME/KEY: MOD_RES
<222> LOCATION: (727)..(727)
<223> OTHER INFORMATION: PHOSPHORYLATION

<400> SEQUENCE: 3

Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
                20                  25                  30

Phe Leu Ala Pro Trp Ile Glu Ser Gln Asp Trp Ala Tyr Ala Ala Ser
            35                  40                  45

Lys Glu Ser His Ala Thr Leu Val Phe His Asn Leu Leu Gly Glu Ile
    50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
                85                  90                  95

Lys Pro Met Glu Ile Ala Arg Ile Val Ala Arg Cys Leu Trp Glu Glu
                100                 105                 110

Ser Arg Leu Leu Gln Thr Ala Ala Thr Ala Ala Gln Gln Gly Gly Gln
            115                 120                 125

Ala Asn His Pro Thr Ala Ala Val Val Thr Glu Lys Gln Gln Met Leu
    130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
                180                 185                 190

Gln Ser Val Thr Arg Gln Lys Met Gln Gln Leu Glu Gln Met Leu Thr
            195                 200                 205
```

-continued

```
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu Gln
        275                 280                 285
Gln Lys Val Ser Tyr Lys Gly Asp Pro Ile Val Gln His Arg Pro Met
    290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
            420                 425                 430
Thr Glu Glu Leu His Leu Ile Thr Phe Glu Thr Glu Val Tyr His Gln
        435                 440                 445
Gly Leu Lys Ile Asp Leu Glu Thr His Ser Leu Pro Val Val Val Ile
    450                 455                 460
Ser Asn Ile Cys Gln Met Pro Asn Ala Trp Ala Ser Ile Leu Trp Tyr
465                 470                 475                 480
Asn Met Leu Thr Asn Asn Pro Lys Asn Val Asn Phe Phe Thr Lys Pro
                485                 490                 495
Pro Ile Gly Thr Trp Asp Gln Val Ala Glu Val Leu Ser Trp Gln Phe
            500                 505                 510
Ser Ser Thr Thr Lys Arg Gly Leu Ser Ile Glu Gln Leu Thr Thr Leu
        515                 520                 525
Ala Glu Lys Leu Leu Gly Pro Gly Val Asn Tyr Ser Gly Cys Gln Ile
    530                 535                 540
Thr Trp Ala Lys Phe Cys Lys Glu Asn Met Ala Gly Lys Gly Phe Ser
545                 550                 555                 560
Phe Trp Val Trp Leu Asp Asn Ile Ile Asp Leu Val Lys Lys Tyr Ile
                565                 570                 575
Leu Ala Leu Trp Asn Glu Gly Tyr Ile Met Gly Phe Ile Ser Lys Glu
            580                 585                 590
Arg Glu Arg Ala Ile Leu Ser Thr Lys Pro Pro Gly Thr Phe Leu Leu
        595                 600                 605
Arg Phe Ser Glu Ser Ser Lys Glu Gly Gly Val Thr Phe Thr Trp Val
    610                 615                 620
```

-continued

```
Glu Lys Asp Ile Ser Gly Lys Thr Gln Ile Gln Ser Val Glu Pro Tyr
625             630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Val Ser Pro Leu Val Tyr
                660                 665                 670

Leu Tyr Pro Asp Ile Pro Lys Glu Glu Ala Phe Gly Lys Tyr Cys Arg
        675                 680                 685

Pro Glu Ser Gln Glu His Pro Glu Ala Asp Pro Gly Ser Ala Ala Pro
        690                 695                 700

Tyr Leu Lys Thr Lys Phe Ile Cys Val Thr Pro Thr Thr Cys Ser Asn
705                 710                 715                 720

Thr Ile Asp Leu Pro Met Ser Pro Arg Thr Leu Asp Ser Leu Met Gln
                725                 730                 735

Phe Gly Asn Asn Gly Glu Gly Ala Glu Pro Ser Ala Gly Gly Gln Phe
                740                 745                 750

Glu Ser Leu Thr Phe Asp Met Asp Leu Thr Ser Glu Cys Ala Thr Ser
        755                 760                 765

Pro Met
    770
```